United States Patent
Albach

(10) Patent No.: US 6,848,906 B2
(45) Date of Patent: Feb. 1, 2005

(54) SYRINGE FOR THE METERED DELIVERY OF DENTAL MATERIALS

(75) Inventor: Andrej Albach, Deutschland (DE)

(73) Assignee: Heraeus Kulzer GmbH & Co. KG, Hanau (DE)

( * ) Notice: Subject to any disclaimer, the term of this patent is extended or adjusted under 35 U.S.C. 154(b) by 193 days.

(21) Appl. No.: 09/995,348

(22) Filed: Nov. 27, 2001

(65) Prior Publication Data

US 2002/0068257 A1 Jun. 6, 2002

(30) Foreign Application Priority Data

Dec. 5, 2000 (DE) .......................................... 100 60 614

(51) Int. Cl.[7] .................................................. A61C 5/04
(52) U.S. Cl. ....................................................... 433/90
(58) Field of Search ...................... 433/89, 90; 604/187, 604/199, 232; 222/324, 325, 327

(56) References Cited

U.S. PATENT DOCUMENTS

| | | | |
|---|---|---|---|
| 2,778,359 A | | 1/1957 | Friedman |
| 3,002,517 A | | 10/1961 | Pitton ............................ 132/85 |
| 3,346,147 A | * | 10/1967 | Higgins et al. ................ 433/90 |
| 3,724,076 A | | 4/1973 | Schmitz ........................... 32/60 |
| 3,767,085 A | * | 10/1973 | Cannon ....................... 222/327 |
| 4,457,712 A | | 7/1984 | Dragan .......................... 433/90 |
| 4,560,352 A | | 12/1985 | Neümeister et al. ........... 433/90 |
| 4,569,662 A | * | 2/1986 | Dragan .......................... 433/89 |
| 4,619,613 A | | 10/1986 | Dragan .......................... 433/90 |
| 4,784,607 A | | 11/1988 | Francois ........................ 433/90 |
| 5,062,832 A | * | 11/1991 | Seghi ............................ 433/89 |
| 5,137,528 A | * | 8/1992 | Crose .......................... 222/327 |
| 5,324,273 A | * | 6/1994 | Discko, Jr. ..................... 433/90 |
| 5,618,273 A | | 4/1997 | Fischer ........................ 604/211 |
| 5,875,928 A | * | 3/1999 | Muller et al. ................ 222/327 |

FOREIGN PATENT DOCUMENTS

| | | | | |
|---|---|---|---|---|
| DE | 2 110 463 | 12/1972 | ............ | A61C/5/04 |
| DE | 3 428 030 | 9/1985 | ............ | A61C/5/04 |
| EP | 0 225 265 | 6/1987 | ............ | A61C/9/00 |
| EP | 0 284 244 | 9/1988 | ............ | A61C/5/00 |
| EP | 0 592 741 B1 | 1/1998 | ........... | B05C/17/01 |

OTHER PUBLICATIONS

English translation of Derwent Abstract of DE 2110463 (Oct. 23, 1986).

* cited by examiner

Primary Examiner—Todd E. Manahan
(74) Attorney, Agent, or Firm—Norris McLaughlin & Marcus PA

(57) ABSTRACT

The invention relates to a syringe for delivering flowable and/or highly viscous materials with a syringe tube, which has an outlet nozzle, a material container, which is disposed therein, a handle, which is disposed at the end of the syringe tube opposite to the outlet nozzle, and a syringe piston, which can be moved through the handle into the syringe tube. A safe operation is assured, even when larger pressures are exerted, owing to the fact that the handle is connected by means of a thread to the syringe tube and the material container has a closed lateral surface around the axis.

6 Claims, 1 Drawing Sheet

SYRINGE FOR THE METERED DELIVERY OF DENTAL MATERIALS

Figure 1:
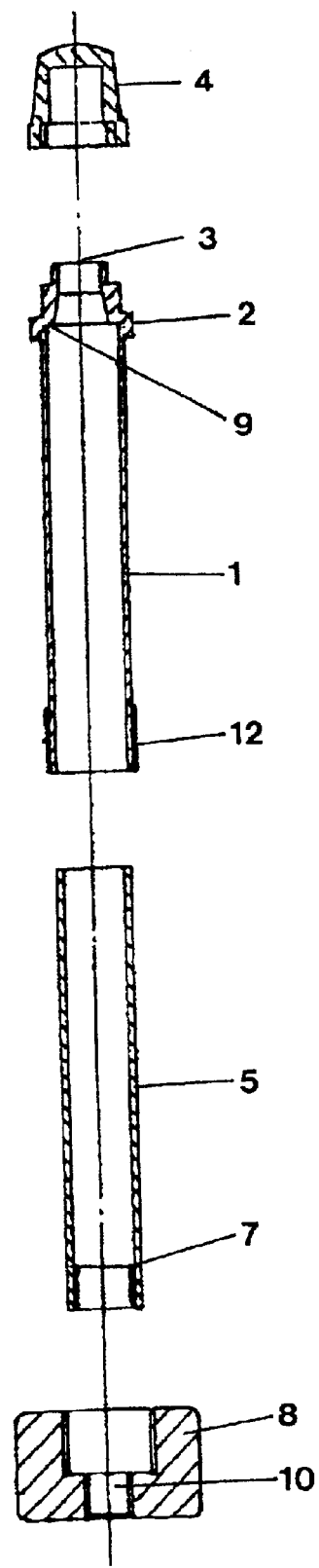

The invention relates to a syringe for delivering flowable and/or highly viscous materials with a syringe tube, which has an outlet nozzle, a material container, which is disposed therein, a handle, which is disposed at the end of the syringe tube opposite to the outlet nozzle, and a syringe piston, which can be moved by the handle into the syringe tube.

Such syringes are already known from the EP 225 265 A1. In this publication, a syringe is disclosed for injecting pasty products, for which a sample tube is disposed in a cylinder, the sample tube having a slot, which encircles a significant portion of its circumference and with the help of which material is scraped from a mixing plate and brought into the cylinder. This material is pressed by means of a sliding piston through the tip of the cylinder and, in this way, injected at the treatment site.

A further syringe for delivering pasty materials is disclosed in the DE 21 10 463 C2 and the DE 34 28 031 A1. These publications disclose syringes for the delivery of dental materials. However, the danger exists here that, when larger pressures are exerted, the outlet nozzle will tear off from the syringe or that the body of the syringe itself will burst.

It is an object of the present invention to make available a syringe, which represents an improvement in comparison to the syringes of the state of the art and can be operated safely even when larger pressures are exerted.

Pursuant to the invention, this objective is accomplished owing to the fact that the handle is disposed on the syringe tube by means of a thread and that the material container has a closed lateral surface around the axis. As a result, the force can be transferred optimally from the syringe piston to the material, which is disposed in the syringe, without any risk that the outlet nozzle will tear off or that a portion of the syringe tube will tear open. The stability and the durability of the syringe are improved by the doubled wall thickness.

In particular, it is advantageous that one end of the material container is disposed at the outlet nozzle and a plug, which can be moved between the two ends, is disposed in the opposite end, the end of the syringe piston, which can be moved into the syringe, being constructed to lie in contact with the plug. As a result, the force is transferred by means of the plug from the syringe piston to the material in the syringe. It is easily possible to construct the plug so that it closes off tightly with the wall of the material container. This seal need not be guaranteed by the syringe piston itself, so that the latter can be constructed more simply and less expensively.

Moreover, it is appropriate that the lateral surface of the material container around the axis is dimensionally stable. The ends of the material container can be open.

In a further advantageous development of the invention, the material container may be constructed from a flexible material, such as a plastic film. At the end of the container, facing the handle, a plug, which can be moved into the syringe tube, may be disposed so that the end of the syringe piston, which can be moved into the syringe, is constructed to lie against the plug. It is, of course, also possible to transfer the pressure from the syringe piston directly to the flexible material, in which case the syringe piston must be constructed in a suitable manner and form a seal with the wall of the syringe tube.

It is furthermore advantageous that the external diameter of the material container is about equal in size to the internal diameter of the syringe tube, so that the two tubes lie in contact with one another with the least possible clearance and reinforce one another. The syringe may be constructed, for example, from a plastic.

It is particularly advisable to construct the syringe body and the outlet nozzle in one piece. For this purpose, both parts can be manufactured by injection molding in a single step. The connection between the outlet nozzle and the syringe tube, which generally is highly stressed when pressure is exerted, is able to absorb the high pressures, which arise during the operation of the syringe, so that a tear does not develop between the syringe and the tube.

The invention furthermore relates to the use of the described syringe for taking up and delivering dental materials.

Figure 2:
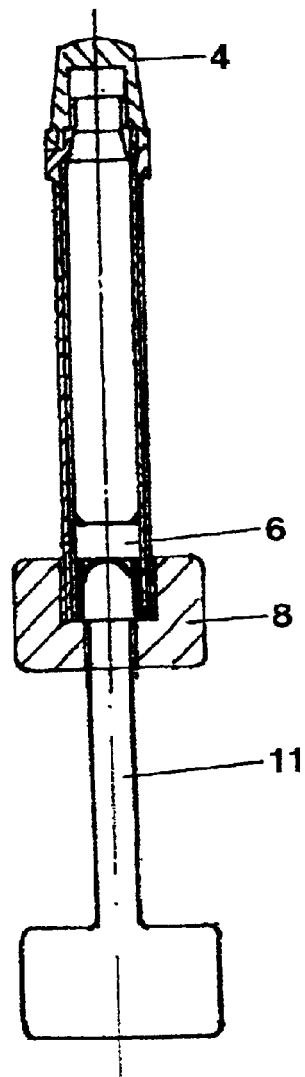

In the following, an example of the invention is described by means of a drawing. The drawing shows an inventive syringe in an exploded representation (FIG. 1) and in an assembled state (FIG. 2), in both cases in section.

An outlet nozzle 2 is disposed monolithically at the syringe tube 1 of a syringe, in that both parts are produced, for example, in one step by injection molding. The outlet nozzle 2 has an outlet opening 3, which varies in size and is adapted to the flowability or viscosity of the material, this adaptation taking place during the injection molding.

The outlet opening 3 is closed off with a cap 4. A plug 6 is inserted in the material container 5 and pushed against a stop 7. After that, the dental material is filled into the material container 5, which is then pushed into the syringe tube 1. At its one end, the syringe tube 1 has a thread 12, into which the handle 8 is screwed. The material container 5 is slightly (a few tenths of a millimeter) longer than the cylindrical inner space of the syringe tube 1, so that its one end protrudes from the syringe tube 1 by this length. As the handle 8 is screwed on, the syringe tube 1 is pressed against the face of the material container 5, so that the latter is pressed firmly against a stop shoulder 9 at the place, where the syringe tube 1 and the outlet nozzle 2 are connected. By these means, it is ensured that material from the material container 5 does not penetrate into a possible space between this material container 5 and the syringe tube 1.

By a threaded borehole 10 in the handle 8, the syringe piston 11 is rotated into the material container 5, until the face of the syringe piston 11 comes up against the plug 6. For extruding the dental material from the syringe, the cap 4 is removed and the syringe piston 11 is screwed further into the material container, so that the dental material is pushed out of the outlet opening 3 by means of the plug 6. The syringe piston 11 may have markings along the thread to indicate the position of the plug 6 within the material container 5 and, with that, to indicate the extent to which the syringe has been emptied. The plug 6 itself can also be integrally molded directly to the syringe piston 11, in which case, the stop 7 of the material container 5 can be omitted.

All parts of this syringe are formed from a dimensionally stable plastic. They may also, however, be formed from metal.

In a further embodiment of the invention, the material container 5 can be constructed from a flexible material, such as a film bag. In this case, after the material container 5 is inserted in the syringe tube 1, the plug 6 is placed positively and directly in the syringe tube 1.

What is claimed is:

1. A syringe for delivering flowable and/or highly viscous materials, comprising a right-cylindrical syringe tube, having an outlet nozzle at a first end thereof, and a second end which is threaded to accommodate a removable handle having complementary threads, a material container disposed therein, a removable handle having a borehole passing through it to communicate with the interior of said syringe tube, one end of said borehole having threads to accommodate said threaded end of said syringe tubes and the other end having threads to accommodate a threaded piston, said handle being threaded onto said second end of said syringe tube, and a syringe piston, one end of which is movable through said borehole in said handle and thence, by rotating the piston under the influence of said threads, into the syringe tube and the material container disposed therein, the other end of said piston projecting outwardly from said syringe said material container having a closed lateral surface around its axis and open ends, said syringe tube and outlet nozzle being of single-piece construction.

2. The syringe of claim 1, wherein one end of the material container is disposed at the outlet nozzle and a plug, which can be moved between the ends, is disposed at the opposite end, the end of the syringe piston, which can be moved into the syringe, being constructed to lie in contact with the plug.

3. The syringe of claim 2, wherein the lateral surface of the material container around the axis is dimensionally stable.

4. The syringe of claim 1, wherein the material container is formed from a flexible material and a plug, which can be moved in the syringe tube, is disposed at the end of the material container facing the handle, the end of the syringe piston, which can be moved into the syringe, being constructed to lie in contact with the plug.

5. The syringe of any one of claim 1, 2, 3 or 4, wherein the external diameter of the material container is about equal in size to the internal diameter of the syringe tube.

6. A method for delivering dental materials, which comprises delivering said dental materials with the syringe of claim 1.

* * * * *

UNITED STATES PATENT AND TRADEMARK OFFICE
CERTIFICATE OF CORRECTION

PATENT NO. : 6,848,906 B2
DATED : February 1, 2005
INVENTOR(S) : Albach

It is certified that error appears in the above-identified patent and that said Letters Patent is hereby corrected as shown below:

<u>Column 2,</u>
Lines 64-65, "tube, having" should read -- tube having --.

<u>Column 3,</u>
Line 4, "said syringe tubes" should read -- said syringe tube --.

Signed and Sealed this

Twenty-eighth Day of March, 2006

JON W. DUDAS
*Director of the United States Patent and Trademark Office*